United States Patent [19]

Sakata et al.

[11] Patent Number: 5,359,036
[45] Date of Patent: Oct. 25, 1994

[54] GROWTH HORMONE-LIKE GLYCOPROTEINS

[75] Inventors: Shusaku Sakata, Kawasaki; Hiroshi Kawauchi, Kesen; Masao Ono, Zushi, all of Japan

[73] Assignee: Nippon Oil Company, Limited, Tokyo, Japan

[21] Appl. No.: 656,566

[22] Filed: Feb. 15, 1991

[30] Foreign Application Priority Data

Feb. 19, 1990 [JP] Japan .................................. 2-36090

[51] Int. Cl.$^5$ ........................ A61K 37/02; C07K 3/00; A23J 1/00; C12P 21/06
[52] U.S. Cl. .................... 530/399; 530/350; 530/395; 530/397; 530/412; 530/413; 530/324; 536/23.1; 435/69.4
[58] Field of Search ............ 435/252.33, 172.3, 320.1, 435/253, 69.4; 536/27; 530/397, 350, 395, 324, 413, 399, 412; 514/2, 12, 21

[56] References Cited

U.S. PATENT DOCUMENTS

| 4,849,359 | 7/1989 | Sekine et al. | 435/252.33 |
| 4,894,362 | 1/1990 | Yamaguchi et al. | 514/12 |

FOREIGN PATENT DOCUMENTS 0213357 3/1987 European Pat. Off. .
0239075 9/1987 European Pat. Off. .

OTHER PUBLICATIONS

Momota, et al. (1988) "Amino Acid Sequence of Flounder Growth Hormone Deduced from a cDNA Sequence", *Nucleic Acids Research*, 16, 10362.

Mori, et al. (1989) "The Complete cDNA Sequence for the Premature Form of Growth Hormone of the Flounder *Paralichthys Olivaceus*", *Nucleic Acids Research*, 17, 3977.

Ono, et al. (1990) "cDNA Cloning of Somatolactin, A Pituitary Protein Related to Growth Hormone and Prolactin", *Proc. Natl. Acad. Sci. USA*, 87, 4330–4334.

Watahiki, et al. (1989) "Conserved and Unique Amino Acid Residues in the Domains of the Growth Hormones", *Journal of Bio. Chem.*, 264, 312–316.

Primary Examiner—Robert J. Hill, Jr.
Assistant Examiner—Gian P. Wang
Attorney, Agent, or Firm—Scully, Scott Murphy & Presser

[57] ABSTRACT

Disclosed herein are methods and means of producing novel growth hormone-like proteins derived from the pituitary gland of fishes belonging to the order Pleuronectina, the family Paralichthydae, which are useful in the growth promotion for fishes, by genetic engineering using cloned genes.

4 Claims, 5 Drawing Sheets

```
      1          10            20            30            40            50            60
      ATG AAC ATG ATG ACA GTC AAG CAG CAG GGT GTA TGG GCT GCG TTG CTC TGG CCC TAT TTG
      Met Asn Met Met Thr Val Lys Gln Gln Gly Val Trp Ala Ala Leu Leu Trp Pro Tyr Leu

-24------------------------signal peptide-------------------------
                  70            80            90           100           110           120
      CTC ACT GCG AGC ATC CCA CTA GAC TGC AAG GAA GAG CAA GGC AGC CTC TCC CGC TGC CCC
      Leu Thr Ala Ser Ile Pro Leu Asp Cys Lys Glu Glu Gln Gly Ser Leu Ser Arg Cys Pro

- - - - - - -1  +1-→N-terminal                 10
                 130           140           150           160           170           180
      TCC ATC TCG CAA GAA AAA CTT CTA GAC CGA GTC ATC CAG CAT GCC GAG CTC ATC TAC CGC
      Ser Ile Ser Gln Glu Lys Leu Leu Asp Arg Val Ile Gln His Ala Glu Leu Ile Tyr Arg
                  20                                         30
                 190           200           210           220           230           240
      GTG TCG GAG GAG TCG TGT TCT ATG TTT GAG GAG ATG TTT GTC CCA TTT CCA CTG CGT CTC
      Val Ser Glu Glu Ser Cys Ser Met Phe Glu Glu Met Phe Val Pro Phe Pro Leu Arg Leu
                  40                                         50
                 250           260           270           280           290           300
      CAG AGG AAC CAG GCT GGC TAT GCA TGC ATC ACC AAA GCC TTA CCC ATC CCC AGC TCC AAA
      Gln Arg Asn Gln Ala Gly Tyr Ala Cys Ile Thr Lys Ala Leu Pro Ile Pro Ser Ser Lys
                  60                                         70
                 310           320           330           340           350           360
      ATG GAA ATC CAG CAG ATA TCT GAT ACA TGG CTG CTC CAC TCC GTG CTG ATG CTG GTC CAG
      Ser Glu Ile Gln Gln Ile Ser Asp Thr Trp Leu Leu His Ser Val Leu Met Leu Val Gln
                  80                                         90
                 370           380           390           400           410           420
      TCG TGG ATC GAG CCC CTG GTC TAC CTG CAG ACT ACG CTA GAT CGC TAC GAC AAC GCT CCG
      Ser Trp Ile Glu Pro Leu Val Tyr Leu Gln Thr Thr Leu Asp Arg Tyr Asp Asn Ala Pro
                 100                                        110
                 430           440           450           460           470           480
      GAC ATG CTC CTC AAC AAG ACC AAG TGG GTG TCT GAC AAA CTG ATC AGT CTG GAG CAA GGG
      Asp Met Leu Leu [Asn Lys Thr] Lys Trp Val Ser Asp Lys Ile Ser Leu Glu Gln Gly
                 120                                        130
                 490           500           510           520           530           540
      GTG GTG GTG CTT ATC AGG AAG ATG TTG GAC GAG GGA ATG TTG ACT GCA ACC TAC AAC GAA
      Val Val Val Leu Ile Arg Lys Met Leu Asp Glu Gly Met Leu Thr Ala Thr Tyr Asn Glu
                 140                                        150
                 550           560           570           580           590           600
      CAA GGC CTG TTC CAG TAT GAT GCG CAG CCA GAT ATG TTG GAA TCG GTG ATG AGA GAC TAT
      Gln Gly Leu Phe Gln Tyr Asp Ala Gln Pro Asp Met Leu Glu Ser Val Met Arg Asp Tyr
                 160                                        170
                 610           620           630           640           650           660
      ACC CTG CTC AGC TGC TTC AAG AAA GAC GCC CAT AAG ATG GAG ATC TTC CTC AAG CTC CTC
      Thr Leu Leu Ser Cys Phe Lys Lys Asp Ala His Lys Met Glu Ile Phe Leu Lys Leu Leu
                 180                                        190
                 670           680           690   696
      AAA TGT CGA CAA ACT GAC AAA TAC AAC TGT GCA TAA
      Lys Cys Arg Gln Thr Asp Lys Tyr Asn Cys Ala ***
                 200                        207
```

```
1           10          20          30          40          50          60
ATG AAC ATG ATG ACA GTC AAG CAG CAG GGT GTA TGG GCT GCG TTG CTC TGG CCC TAT TTG
Met Asn Met Met Thr Val Lys Gln Gln Gly Val Trp Ala Ala Leu Leu Trp Pro Tyr Leu

-24--------------------------------------signal peptide-------------------------
            70          80          90          100         110         120
CTC ACT GCG AGC ATC CCA CTA GAC TGC AAG GAA GAG CAA GGC AGC CTC TCC CGC TGC CCC
Leu Thr Ala Ser Ile Pro Leu Asp Cys Lys Glu Glu Gln Gly Ser Leu Ser Arg Cys Pro

- - - - - - -1  +1→N - t e r m i n a l         10
            130         140         150         160         170         180
TCC ATC TCG CAA GAA AAA CTT CTA GAC CGA GTC ATC CAG CAT GCC GAG CTC ATC TAC CGC
Ser Ile Ser Gln Glu Lys Leu Leu Asp Arg Val Ile Gln His Ala Glu Leu Ile Tyr Arg
            20                                  30
            190         200         210         220         230         240
GTG TCG GAG GAG TCG TGT TCT ATG TTT GAG GAG ATG TTT GTC CCA TTT CCA CTG CGT CTC
Val Ser Glu Glu Ser Cys Ser Met Phe Glu Glu Met Phe Val Pro Phe Pro Leu Arg Leu
            40                                  50
            250         260         270         280         290         300
CAG AGG AAC CAG GCT GGC TAT GCA TGC ATC ACC AAA GCC TTA CCC ATC CCC AGC TCC AAA
Gln Arg Asn Gln Ala Gly Tyr Ala Cys Ile Thr Lys Ala Leu Pro Ile Pro Ser Ser Lys
            60                                  70
            310         320         330         340         350         360
ATG GAA ATC CAG CAG ATA TCT GAT ACA TGG CTG CTC CAC TCC GTG CTG ATG CTG GTC CAG
Ser Glu Ile Gln Gln Ile Ser Asp Thr Trp Leu Leu His Ser Val Leu Met Leu Val Gln
            80                                  90
            370         380         390         400         410         420
TCG TGG ATC GAG CCC CTG GTC TAC CTG CAG ACT ACG CTA GAT CGC TAC GAC AAC GCT CCG
Ser Trp Ile Glu Pro Leu Val Tyr Leu Gln Thr Thr Leu Asp Arg Tyr Asp Asn Ala Pro
            100                                 110
            430         440         450         460         470         480
GAC ATG CTC CTC AAC AAG ACC AAG TGG GTG TCT GAC AAA CTG ATC AGT CTG GAG CAA GGG
Asp Met Leu Leu |Asn Lys Thr| Lys Trp Val Ser Asp Lys Leu Ile Ser Leu Glu Gln Gly
            120                                 130
            490         500         510         520         530         540
GTG GTG GTG CTT ATC AGG AAG ATG TTG GAC GAG GGA ATG TTG ACT GCA ACC TAC AAC GAA
Val Val Val Leu Ile Arg Lys Met Leu Asp Glu Gly Met Leu Thr Ala Thr Tyr Asn Glu
            140                                 150
            550         560         570         580         590         600
CAA GGC CTG TTC CAG TAT GAT GCG CAG CCA GAT ATG TTG GAA TCG GTG ATG AGA GAC TAT
Gln Gly Leu Phe Gln Tyr Asp Ala Gln Pro Asp Met Leu Glu Ser Val Met Arg Asp Tyr
            160                                 170
            610         620         630         640         650         660
ACC CTG CTC AGC TGC TTC AAG AAA GAC GCC CAT AAG ATG GAG ATC TTC CTC AAG CTC CTC
Thr Leu Leu Ser Cys Phe Lys Lys Asp Ala His Lys Met Glu Ile Phe Leu Lys Leu Leu
            180                                 190
            670         680         690         696
AAA TGT CGA CAA ACT GAC AAA TAC AAC TGT GCA TAA
Lys Cys Arg Gln Thr Asp Lys Tyr Asn Cys Ala ***
            200                     207
```

FIG.4

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 23 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:1:

```
Ile  Pro  Leu  Asp  Cys  Lys  Glu  Glu  Gln  Gly  Ser  Leu  Ser  Arg  Cys  Pro
 1                  5                        10                            15

Ser  Ile  Ser  Gln  Glu  Lys  Leu
               20
```

( 2 ) INFORMATION FOR SEQ ID NO:2:

(i) SEQUENCE CHARACTERISTICS:
   (A) LENGTH: 207 amino acids
   (B) TYPE: amino acid
   (D) TOPOLOGY: linear (ii) MOLECULE TYPE: protein (xi) SEQUENCE DESCRIPTION: SEQ ID NO:2:

```
Ile Pro Leu Asp Cys Lys Glu Glu Gln Gly Ser Leu Ser Arg Cys Pro
 1               5                  10                  15

Ser Ile Ser Gln Glu Lys Leu Leu Asp Arg Val Ile Gln His Ala Glu
                20                  25                  30

Leu Ile Tyr Arg Val Ser Glu Glu Ser Cys Ser Met Phe Glu Glu Met
            35                  40                  45

Phe Val Pro Phe Pro Leu Arg Leu Gln Arg Asn Gln Ala Gly Tyr Ala
        50                  55                  60

Cys Ile Thr Lys Ala Leu Pro Ile Pro Ser Ser Lys Ser Glu Ile Gln
65                      70                  75                  80

Gln Ile Ser Asp Thr Trp Leu Leu His Ser Val Leu Met Leu Val Gln
                85                  90                  95

Ser Trp Ile Glu Pro Leu Val Tyr Leu Gln Thr Thr Leu Asp Arg Tyr
                100                 105                 110

Asp Asn Ala Pro Asp Met Leu Leu Asn Lys Thr Lys Trp Val Ser Asp
            115                 120                 125

Lys Leu Ile Ser Leu Glu Gln Gly Val Val Val Leu Ile Arg Lys Met
    130                 135                 140

Leu Asp Glu Gly Met Leu Thr Ala Thr Tyr Asn Glu Gln Gly Leu Phe
145                 150                 155                 160

Gln Tyr Asp Ala Gln Pro Asp Met Leu Glu Ser Val Met Arg Asp Tyr
                165                 170                 175

Thr Leu Leu Ser Cys Phe Lys Lys Asp Ala His Lys Met Glu Ile Phe
            180                 185                 190

Leu Lys Leu Leu Lys Cys Arg Gln Thr Asp Lys Tyr Asn Cys Ala
    195                 200                 205
```

(2) INFORMATION FOR SEQ ID NO:3:

(i) SEQUENCE CHARACTERISTICS:
   (A) LENGTH: 231 amino acids
   (B) TYPE: amino acid
   (D) TOPOLOGY: linear (ii) MOLECULE TYPE: protein (xi) SEQUENCE DESCRIPTION: SEQ ID NO:3:

```
Met Asn Met Met Thr Val Lys Gln Gln Gly Val Trp Ala Ala Leu Leu
 1               5                  10                  15

Trp Pro Tyr Leu Leu Thr Ala Ser Ile Pro Leu Asp Cys Lys Glu Glu
                20                  25                  30

Gln Gly Ser Leu Ser Arg Cys Pro Ser Ile Ser Gln Glu Lys Leu Leu
            35                  40                  45

Asp Arg Val Ile Gln His Ala Glu Leu Ile Tyr Arg Val Ser Glu Glu
        50                  55                  60

Ser Cys Ser Met Phe Glu Glu Met Phe Val Pro Phe Pro Leu Arg Leu
65                  70                  75                  80

Gln Arg Asn Gln Ala Gly Tyr Ala Cys Ile Thr Lys Ala Leu Pro Ile
                85                  90                  95

Pro Ser Ser Lys Ser Glu Ile Gln Gln Ile Ser Asp Thr Trp Leu Leu
                100                 105                 110

His Ser Val Leu Met Leu Val Gln Ser Trp Ile Glu Pro Leu Val Tyr
```

|     |     |     |     |     | 115 |     |     |     |     | 120 |     |     |     |     | 125 |     |     |
|-----|-----|-----|-----|-----|-----|-----|-----|-----|-----|-----|-----|-----|-----|-----|-----|-----|-----|
| Leu | Gln | Thr | Thr | Leu | Asp | Arg | Tyr | Asp | Asn | Ala | Pro | Asp | Met | Leu | Leu |
|     | 130 |     |     |     |     | 135 |     |     |     |     | 140 |     |     |     |     |
| Asn | Lys | Thr | Lys | Trp | Val | Ser | Asp | Lys | Leu | Ile | Ser | Leu | Glu | Gln | Gly |
| 145 |     |     |     |     | 150 |     |     |     |     | 155 |     |     |     |     | 160 |
| Val | Val | Val | Leu | Ile | Arg | Lys | Met | Leu | Asp | Glu | Gly | Met | Leu | Thr | Ala |
|     |     |     |     | 165 |     |     |     |     | 170 |     |     |     |     | 175 |     |
| Thr | Tyr | Asn | Glu | Gln | Gly | Leu | Phe | Gln | Tyr | Asp | Ala | Gln | Pro | Asp | Met |
|     |     |     | 180 |     |     |     |     | 185 |     |     |     |     | 190 |     |     |
| Leu | Glu | Ser | Val | Met | Arg | Asp | Tyr | Thr | Leu | Leu | Ser | Cys | Phe | Lys | Lys |
|     |     | 195 |     |     |     |     | 200 |     |     |     |     | 205 |     |     |     |
| Asp | Ala | His | Lys | Met | Glu | Ile | Phe | Leu | Lys | Leu | Leu | Lys | Cys | Arg | Gln |
|     | 210 |     |     |     |     | 215 |     |     |     |     | 220 |     |     |     |     |
| Thr | Asp | Lys | Tyr | Asn | Cys | Ala |
| 225 |     |     |     |     | 230 |     |

( 2 ) INFORMATION FOR SEQ ID NO:4:

( i ) SEQUENCE CHARACTERISTICS:
        ( A ) LENGTH: 696 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
ATGAACATGA TGACAGTCAA GCAGCAGGGT GTATGGGCTG CGTTGCTCTG GCCCTATTTG      60
CTCACTGCGA GCATCCCACT AGACTGCAAG GAAGAGCAAG GCAGCCTCTC CCGCTGCCCC     120
TCCATCTCGC AAGAAAAACT TCTAGACCGA GTCATCCAGC ATGCCGAGCT CATCTACCGC     180
GTGTCGGAGG AGTCGTGTTC TATGTTTGAG GAGATGTTTG TCCCATTTCC ACTGCGTCTC     240
CAGAGGAACC AGGCTGGCTA TGCATGCATC ACCAAAGCCT TACCCATCCC CAGCTCCAAA     300
AGTGAAATCC AGCAGATATC TGATACATGG CTGCTCCACT CCGTGCTGAT GCTGGTCCAG     360
TCGTGGATCG AGCCCCTGGT CTACCTGCAG ACTACGCTAG ATCGCTACGA CAACGCTCCG     420
GACATGCTCC TCAACAAGAC CAAGTGGGTG TCTGACAAAC TGATCAGTCT GGAGCAAGGG     480
GTGGTGGTGC TTATCAGGAA GATGTTGGAC GAGGGAATGT TGACTGCAAC CTACAACGAA     540
CAAGGCCTGT TCCAGTATGA TGCGCAGCCA GATATGTTGG AATCGGTGAT GAGAGACTAT     600
ACCCTGCTCA GCTGCTTCAA GAAAGACGCC CATAAGATGG AGATCTTCCT CAAGCTCCTC     660
AAATGTCGAC AAACTGACAA ATACAACTGT GCATAA                               696
```

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
ATGATCCCAC TAGACTGCAA GGAAGAGCAA GGCA                                 34
```

GROWTH HORMONE-LIKE GLYCOPROTEINS

FIELD OF THE INVENTION

This invention relates to a novel growth hormone-like protein derived from pituitary gland or hypophysis of fishes, and, more particularly, to a growth hormone-like glycoprotein derived from pituitary gland of fishes belonging to the order Pleuronectina, the family Paralichthydae, a gene coding its amino acid sequence, a recombinant vector integrating said gene, a transformant transformed by said recombinant vector, a new growth hormone-like protein produced by utilizing said transformant and a process for producing the same.

This invention also relates to a process of growth promotion for animals including fishes using the said new growth hormone-like protein.

BACKGROUND OF THE INVENTION

A number of growth hormones for fishes to mammals has been currently isolated and many of them has been elucidated in regard to even the structure of genes thereof, as there growth hormones could have a growth promotion effect so that they are expectable to be applied to growth promotion of fishes and domestic animals, increase in their edible portions in the field of fish farming and livestock raising. And further a growth hormone has been developed in human beings to exert such effects as usefulness in the treatment of dwarfism or nanism, upon which there have been made research and developement to obtain in large amount of such a growth hormone.

However, it was maintained in the report by T. Bistrizer et al. (The Lancet, 13, 321–323 (1988)) and other that there could be present other growth factors than growth hormones, in view of the presence of individuals showing a normal growth even under a deficient condition of growth hormones.

Then, the present inventors have made earnest studies upon their considerations that there may be found any growth factor having a higher effect than the prior growth hormones or any hormone having new physiological activities, and that there may be not only a great scientific development but also a higher industrial usefulness if such a substance could be found and obtained in a large amount. As a result of these studies, they have found out a novel growth hormone-like glycoprotein from the pituitary gland of flounder or halibut and further developed a process for producing the same in a large amount, with a successful cloning of the gene coding the amino acid sequence of such a growth hormone-like glycoprotein.

SUMMARY OF THE INVENTION

It has been found that there is a novel growth hormone-like glycoprotein in the pituitary gland of fishes belonging to the order Pleuronectina, the family Paralichthydae, in particular, flounders, which can be isolated and purified, and there can be obtained a gene which codes the amino acid sequence and the sugar chain addition site of said growth hormone-like glycoprotein and the gene can be successfully expressed by cloning the gene by means of a gene recombination technique and the desired growth hormone-like protein in a high purity can be easily produced in a large amount. This invention has been further completed by confirming that both the growth hormone-like glycoprotein obtained from the pituitary gland as described above and the growth hormone-like protein obtained according to a gene recombination technique as described above can exert a satisfactory growth promoting activity on animals, in particular, fishes.

According to this invention, there is provided a novel growth hormone-like protein derived from pituitary gland or hypophysis of fishes, and, more particularly, a growth hormone-like glycoprotein derived from pituitary gland of fishes belonging to the order Pleuronectina, the family Paralichthydae, a gene coding its amino acid sequence, a recombinant vector integrating said gene, a transformant transformed by said recombinant vector, a new growth hormone-like protein produced by utilizing said transformant and a process for producing the same.

This invention also relates to a process of growth promotion for animals including fishes using the said new growth hormone-like protein.

BRIEF DESCRIPTION OF THE DRAWINGS

FIG. 4 shows the DNA base sequence and amino acid sequence for the coding the present growth hormone-like glycoprotein, wherein the open rectangle shows the site of sugar chain to be added.

DETAILED DESCRIPTION OF THE INVENTION

Figure 1:
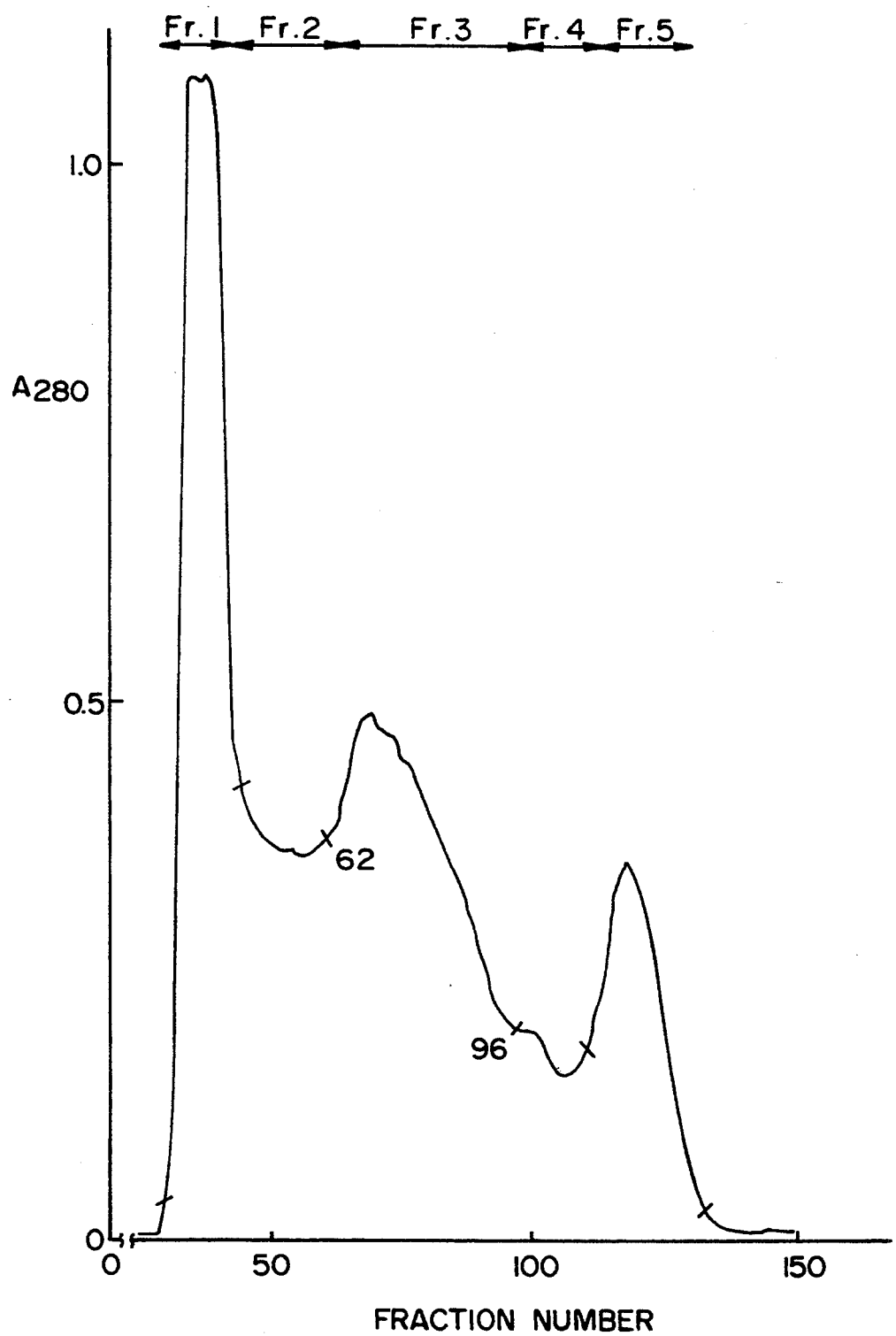
FIG. 1 shows the elution pattern for growth hormone-like glycoprotein by a Sephadex G-J00 column chromatography.

The present invention provides growth hormone-like proteins derived from the pituitary gland of fishes belonging to the order Pleuronectina, the family Paralichthydae, more specifically Paralichthys, genes which code for the amino acid sequence of the above growth hormone-like protein, recombinant vectors integrated with said gene and transformants containing said recombinant vector integrated with said gene.

The present invention further provides processes for producing growth hormone-like proteins derived from the pituitary gland of fishes belonging to the order Pleuronectina, the family Paralichthydae which comprises incubating and multiplying the transformant transformed by the recombinant vector, said vector being integrated with the gene coding for the amino acid sequence of the said growth hormone-like protein, and recovering the said growth hormone-like protein as produced, and processes of growth promotion for fishes which comprises feeding fishes with the said growth hormone-like protein to promote growth of fishes.

The present invention provides specifically growth hormone-like proteins which are growth hormone-like glycoproteins having the following physicochemical properties;

(1) Molecular weight: SDS-PAGE about 28,000 daltons, (2) Isoelectric point: Isoelectric point-PAGE 6.5, (3) Amino acid composition (residues per mole)

| Amino acid | Residue number | Amino acid | Residue number |
|---|---|---|---|
| Cys | 7.0 | Pro | 9.6 |
| Asp | 21.8 | Tyr | 6.9 |
| Glu | 30.1 | Val | 10.3 |
| Ser | 17.3 | Met | 7.6 |
| His | 6.4 | Ile | 12.0 |
| Gly | 2.9 | Leu | 29.3 |
| Arg | 8.9 | Phe | 6.2 |
| Thr | 8.8 | Trp | ... |
| Ala | 9.6 | Lys | 12.8 |

(4) 23 amino acid residues at N-terminal end having the following sequence SEQ ID NO: 1:

Ile—Pro—Leu—Asp—Cys—Lys—
Glu—Glu—Gln—Gly—Ser—Leu—
Ser—Arg—Cys—Pro—Ser—Ile—
Ser—Gln—Glu—Lys—Leu.

The present invention further provides growth hormone-like proteins which are polypeptides obtained by a gene recombination procedure, contain the following amino acid sequence SEQ ID NO: 2 in the molecule and have a growth hormone-like activity:

| Ile 1 | Pro | Leu | Asp | Cys | Lys |
| Glu | Glu | Gln | Gly 10 | Ser | Leu |
| Ser | Arg | Cys | Pro | Ser | Ile |
| Ser | Gln 20 | Glu | Lys | Leu | Leu |
| Asp | Arg | Val | Ile | Gln | His 30 |
| Ala | Glu | Leu | Ile | Tyr | Arg |
| Val | Ser | Glu | Glu 40 | Ser | Cys |
| Ser | Met | Phe | Glu | Glu | Met |
| Phe | Val 50 | Pro | Phe | Pro | Leu |
| Arg | Leu | Gln | Arg | Asn | Gln 60 |
| Ala | Gly | Tyr | Ala | Cys | Ile |
| Thr | Lys | Ala | Leu 70 | Pro | Ile |
| Pro | Ser | Ser | Lys | Ser | Glu |
| Ile | Gln 80 | Gln | Ile | Ser | Asp |
| Thr | Trp | Leu | Leu | His | Ser 90 |
| Val | Leu | Met | Leu | Val | Gln |
| Ser | Trp | Ile | Glu 100 | Pro | Leu |
| Val | Tyr | Leu | Gln | Thr | Thr |
| Leu | Asp 110 | Arg | Tyr | Asp | Asn |
| Ala | Pro | Asp | Met | Leu | Leu 120 |
| Asn | Lys | Thr | Lys | Trp | Val |
| Ser | Asp | Lys | Leu 130 | Ile | Ser |
| Leu | Glu | Gln | Gly | Val | Val |
| Val | Leu 140 | Ile | Arg | Lys | Met |
| Leu | Asp | Glu | Gly | Met | Leu 150 |
| Thr | Ala | Thr | Tyr | Asn | Glu |
| Gln | Gly | Leu | Phe 160 | Gln | Tyr |
| Asp | Ala | Gln | Pro | Asp | Met |
| Leu | Glu 170 | Ser | Val | Met | Arg |
| Asp | Tyr | Thr | Leu | Leu | Ser 180 |
| Cys | Phe | Lys | Lys | Asp | Ala |
| His | Lys | Met | Glu 190 | Ile | Phe |
| Leu | Lys | Leu | Leu | Lys | Cys |
| Arg | Gln 200 | Thr | Asp | Lys | Tyr |
| Asn | Cys | Ala. 207 | | | |

A representative polypeptide has the amino acid sequence SEQID NO: 3 as shown in FIG. 4.

A representative gene which codes for the amino acid sequence of the growth hormone-like protein derived from the pituitary gland of fishes belonging to the order Pleuronectina, the family Paralichthydae is DNA having the base sequence SEQ ID NO: 4 as shown in FIG. 4.

Another representative gene which codes for the amino acid sequence of the growth hormone-like protein derived from the pituitary gland of fishes belonging to the order Pleuronectina, the family Paralichthydae is a synthetic DNA corresponding to the amino acid sequence from the 5th to 22nd from N-terminal end, of the amino acid sequence of the growth hormone-like protein derived from the pituitary gland of fishes belonging to the order Pleuronectina, the family Paralichthydae.

The growth hormone-like glycoproteins according to the present invention can be isolated and purified according to various methods as described below.

The said method may be accomplished, for instance, by applying a method which is known for isolation and purification of a variety of proteins, starting from the tissues or cells containing the above-mentioned growth hormone-like glycoprotein, for example, the pituitary gland of flounders, i.e. fishes belonging to the order Pleuronectina, the family Paralichthydae.

As the methods for the isolation and purification of proteins, there may be mentioned solubilization by a homogenizer, ultrasonic cell breaking and the like; extraction with a buffer containing various salts; solubilization or precipitation with an acid or alkali; extraction or precipitation with an organic solvent, salting-out with ammonum sulfate and the like; dialysis; ultrafiltration using a membrane filter and the like; gel filtration chromatography; ion exchange chromatography; reversed-phase chromatography; countercurrent chromatography; high performance liquid chromatography; isoelectric point; or gel electrophoresis and so on and they may be employed alone or in any optional combination therewith.

A method for the isolation and purification of the present growth hormone-like glycoprotein may be illustrated in detail as below. The pituitary gland was obtained from flounder in a conventional manner, immediately frozen by using liquid nitrogen or dry ice and stored at about −80° C. up to its use. Then, the pituitary gland is minced under cooling, defatted using an organic solvent, e.g. acetone and then centrifuged. The precipitate thus obtained is suspended in a buffer in the presence of an inhibition for a proteolytic enzyme and alkali-extracted with an alkali, e.g. sodium hydroxide. The extract is centrifuged, where necessary, dialyzed and then freeze-dried.

Then, the product thus is dissolved in a suitable buffer and then subjected to gel filtration chromatography, e.g. charomatography with a Sephadex G-J100 column. The fractions as eluted can be measured and collected by monitoring the absorbance at 280 nm. Then, of the fractions thus obtained, the desired fractions containing growth hormone-like glycoprotein are freeze-dried.

Then, the product thus obtained is dissolved in a suitable buffer and then subjected to a high performance liquid chromatography (HPLC), for example, a high performance liquid chromatography using a chemically modified silica gel such as ODS 120T and others as a carrier. The fractions containing the desired growth hormone-like glycoprotein are collected by monitoring the eluates with the absorbance at 220 nm.

The growth hormone-like glycoprotein thus produced can be determined for its properties according to the various physicochemical analyses.

The present growth hormone-like glycoprotein can be be presumed to have a molecular weight of approximately 28,000 daltons as a result of electrophoresis with SDB polyacrylamide gel. And further, the protein obtained by the said high speed liquid chromatography produces a single band in electrophoresis with SDS polyacrylamide gel.

The present growth hormone-like glycoprotein is also presumed to show an isoelectric point of 6.5 in electrophoresis for isoelectric point.

The growth hormone-like glycoprotein thus isolated and purified as above is hydrolyzed with an acid, e.g. hydrochloric acid and the like or a proteolytic enzyme, e.g. pepsin, trypsin, chymotrypsin, carboxypeptidase and the like and the peptide fragments thus obtained can be then separated by a chromatography, e.g. an ion exchange chromatography and the like and each peptide fragment can be analyzed for its amino acid composition and also determined its amino acid sequence by means of an amino acid auto analyzer and others.

Analysis for the amino acid composition of the present growth hormone-like glycoprotein is, more illustratively, to hydrolyze first the purified growth hormone-like glycoprotein with hydrochloric acid, react with phenyl isothiocyanate (PITC) to convert the amino acids to the corresponding phenylthiocarbamyl derivatives and quantitatively determine the derivatives by a reversed-phase high performance liquid chromatography (PITC method).

The amino acid composition of the present growth hormone-like glycoprotein as determined above is as shown in Table 1.

TABLE 1

| Amino Acid Composition (residues per mole) | | | |
|---|---|---|---|
| Amino acid | Residue number | Amino acid | Residue number |
| Cys | 7.0 | Pro | 9.6 |
| Asp | 21.8 | Tyr | 6.9 |
| Glu | 30.1 | Val | 10.3 |
| Ser | 17.3 | Met | 7.6 |
| His | 6.4 | Ile | 12.0 |
| Gly | 2.9 | Leu | 29.3 |
| Arg | 8.9 | Phe | 6.2 |
| Thr | 8.8 | Trp | ... |
| Ala | 9.6 | Lys | 12.8 |

As seen from this Table, the present growth hormone-like glycoprotein has the growth hormone-like properties in that it has 7 cysteines and is rich in glutamic acid, leucine and serine.

In order to determine the amino acid sequence of the present growth hormone-like glycoprotein, one may employ any usual peptide sequencer, a gas-phase peptide sequencer being particularly preferred.

According to such a peptide sequencer, one may determine the amino acid sequence from N-terminal of the said protein.

The sequence of 23 amino acid residues (SEQ ID NO: 1) at N-terminal end of the present growth hormone-like glycoprotein as determined according to such procedures is as shown below.

Ile—Pro—Leu—Asp—Cys—Lys—
Glu—Glu—Gln—Gly—Ser—Leu—
Ser—Arg—Cys—Pro—Ser—Ile—
Ser—Gln—Glu—Lys—Leu.

The gene, which may code for the amino acid sequence of the present growth hormone-like glycoprotein, may be prepared according to a variety of methods as disclosed below.

As the said methods, there may be mentioned, for instance, a method wherein poly(A)RNA is prepared from the pituitary gland of flounder, fishes belonging to the order Pleuronectina, the family Paralichthydae, which is producing cell for the above-mentioned growth hormone-like glycoprotein, cDNA is synthesized by using the poly(A)RNA as a template and multiplied in host cells with a suitable vector, a clone is selected which contains cDNA coding for the aimed amino acid sequence of the growth hormone-like glycoprotein and the gene is isolated from the vector of said clone; a method wherein a suitable DNA probe is synthesized upon the finding obtained as a result of the amino acid sequence analysis of the growth hormone-like glycoprotein obtained from fishes according to the present isolation and purification method, a gene library is investigated using such a probe to select the clone containing cDNA coding for the amino acid sequence of the desired growth hormone-like glycoprotein and the corresponding gene is isolated from said clone; a method wherein a nucleic acid is chemically synthesized upon DNA of the gene coding for the amino acid sequence of the present growth hormone-like glycoprotein according to a conventional method, for example, a phosphotriester method (Tetrahedron, 34, 3153 (1978), Adv. Carbohydr. Chem. Boiochem., 36, 135 (1979), Nucleic Acids Res., 10, 2597, 6553 (1982)), a phosphoramidite method (Nature, 310, 105 (1984)) and others; or any combination of these methods.

A method for preparing the said gene from the above flounder pituitary gland will be illustrated in detail below.

In order to obtain the gene of this invention, it is necessary to extract RNA from flounder pituitary gland, and one may preferably employ any of raised and natural flounder. The pituitary gland may be isolated from flounders in a conventional manner and the pituitary gland thus isolated is immediately frozen by the use of liquid nitrogen, dry ice.acetone and the like and, as required, may be stored at about −80° C. until it is to be used.

From the pituitary gland obtained as above, RNA may be extracted in a conventional manner, which may include separation of polysome, utilization of sucrose density gradient centrifugation or electrophoresis. As the extraction method for RNA from the said pituitary gland, there may be mentioned a guanidine.thiocyanate—cesium chloride method wherein CsCl density gradient centrifugation is effected after treatment with guanidine.thiocyanate (Chirgwin, et al., Biochemistry, 18, 5294 (1979); a method which comprises treating with a surface active agent in the presence of an inhibitor of ribonuclease using a vanadium complex and then treating with phenol (Berger, et al., Biochemistry, 18, 5143 (1979); a guanidine.thiocyanate—hot phenol method; a guanidine.thiocyanate—guanidine hydrochloric acid method; a guanidine.thiocyanate—phenol.-chloroform method; a method which comprises treating with guanidine.thiocyanate and then treating with lithium chloride to precipitate RNA; and others.

The RNA extraction method from the said pituitary gland will be illustrated in detail as below.

The frozen pituitary gland may be first solubilized by mechanically mincing in a guanidine.thiocyanate solution, lithium chloride is then added and, where necessary, centrifugation is done to obtain cellular RNA as precipitate. Thereafter, the precipitate thus obtained may be, where necessary, extracted with phenol and then precipitated with ethanol to give RNA as a precipitate.

From the RNA thus obtained, one may further purify the RNA having a polyA chain in a conventional manner. As such method, there may be advantageously employed an affinity column chromatography using oligo-dT cellulose and others.

The poly(A)RNA thus obtained may be employed as a template for the synthesis of a double-stranded DNA (cDNA) using a reverse transcriptase. The cDNA may be synthesized according to any conventional methods. First, the first stranded DNA is synthesized with oligo(dT) or vector primer as a primer using, for example, any reverse transcriptase derived from, e.g. AMV, MMLV, RSV and the like and then treated with Klenow fragment to form the double-stranded DNA. Then, it is treated with T4 DNA ligase and then with S1 nuclease or treated with S1 nuclease and then with terminal transferase. Alternatively, the first stranded DNA-containing product obtained using the said reverse transcriptase is subjected to action by DNA polymerase I, robonuclease H and E. coli DNA ligase. As such methods, there may be mentioned those as disclosed in Methods in Enzymology, Vol. 152, 307~335, Ed. by Shelby L. Barget et al., Academic Press, Inc. (1987), but it is practically convenient for this cDNA synthesis to utilize any cDNA synthesis kits commercially available form, e.g. Amersham Japan Ltd.

The cDNA thus obtained may be inserted into a suitable vector which is then amplified by introducing into a suitable host and cloning, a recombinant host containing cDNA coding for the amino acid sequence of the desired growth hormone-like glycoprotein is selected by conducting a screening and then the DNA coding for the amino acid sequence of the said growth hormone-like glycoprotein can be isolated from the plaque or colony of such recombinant host.

As the vector which may be employed for insertion of the said cDNA, there may be mentioned a variety of plasmid vectors commonly employed, and one may preferably employ, for example, pBR322, λ bacteriophage vectors, λ gt 10, λ gt 11 and the like.

And there is no particular limitation to the host which may be employed herein, provided that the said recombinant vector may accomplish autoreplication, and, for example, E. coli may be preferably employed as the host. Particularly when λ gt 10 DNA is employed as the said vector, E. coli NM514 strain may be preferably employed as a host.

In inserting the said cDNA into a vector, there may be employed any conventional methods in which a restriction site produced by using the identical restriction enzyme is utilized, any synthetic linker or adaptor is added where necessary or a homopolymer is added.

For instance, more specifically, EcoRI linker may be added to cDNA at both terminal ends using T4 ligase, digestion is done with restriction enzyme EcoRI, and the vector fragment digested with the same restriction enzyme EcoRI is ligated, thereby the desired recombinant vector being obtained.

The recombinant vector thus obtained may be introduced into a host by any methods commonly employed.

As the methods, there may be mentioned, for example, a method wherein the vector may be incorporated into competent cells prepared in the co-existence of $CaCl_2$ or RbCl according to Hanahan et al., J. Mol. Biol 166, 557 (1983); a method wherein the host in a suitable propagative phase is treated with $MgSO_4$ and the like and then a recombinant phage vector is infected; and others.

Thereafter, the recombinant containing DNA coding for the amino acid sequence of the growth hormone-like glycoprotein is selected by screening. In this selection, there may be applied any well-known various methods, for example, a colony or plaque hybridization method using chemically synthesized oligonucleotide probe; a hybridization.translation assay method; a plus-minus method; and others may be advantageously applied.

More specifically, the DNA of the recombinant plaque is fixed on a filter of, e.g. a nylon membrane and then reacted with a labeled probe to select a recombinant having the DNA sequence to be selectively bound to the said probe.

The probe as used herein is indicated to be a nucleic acid sequence having a complementary sequence to the aimed DNA sequence and it may be RNA or DNA and of a chemically synthesized or natural type or of a type obtained according to a recombinant DNA procedure. The said DNA sequence as chemically synthesized by application of well-known methods may be generally and preferably employed.

In synthesizing the probe DNA sequence chemically, the sequence may be determined upon the amino acid sequence of the aimed growth hormone-like glycoprotein, in particular, the amino acid sequence of the flounder growth hormone-like glycoprotein.

The DNA base sequence of the gene according to this invention as obtained from the selected recombinant as above may be determined according to Maxam-Gilbert method, Dideoxy method, e.g. dideoxynucleotide chain termination method (Sanger, Science, 214, 1205 (1981); Methods in Enzymology, 65, 560-580 (1980); Messing. J. et al., Nucleic Acids Res., 9, 309 (1981) and others.

The DNA sequence SEQ ID NO: 4 and amino acid sequence SEQID NO: 3, which contain the gene of the present growth hormone-like glycoprotein, particularly, the growth hormone-like glycoprotein derived from flounder, as determined above are as shown in FIG. 4. The sequence includes the DNA sequence and amino acids of the precursor for the growth hormone-like glycoprotein from flounder. In this DNA sequence, the first to 72nd amino acid sequence sites correspond to signal peptides, while the 73rd to 693rd amino acid sequence sites correspond to mature proteins. It has been elucidated that said growth hormone-like glycoprotein from flounders is first bio-synthesized as the said precursor and then the signal peptide sites are removed to form secretory proteins.

The amino acid sequence determined upon this DNA sequence is in perfect agreement with the amino acid sequence of the said growth hormone-like glycoprotein already determined upon the natural product and hence the said cDNA obtained from the recombinant has been confirmed to code for the amino acid sequence of the growth hormone-like glycoprotein from flounder.

Also, the DNA base sequence has been confirmed to have a significant homology with those growth hormones discovered in the past such as prolactin etc. and, especially, a significant homology with the growth hormone of rat, mammals.

According to gene recombination techinques, there can be carried out deletion, insertion, addition and ligation of DNA chains including even substitution of bases in DNA chains in a conventional manner and, therefore, the present gene relates not only to the gene having the base sequence as shown in FIG. 4, but also to alterations and modifications thereof as mentioned above within the scope not departing from the present objects.

The most preferred alteration and modification of the gene having the base sequence shown in FIG. 4, which fall within the present scope, may be an increase in stability and biological activity of the aimed protein.

The present gene coding for the amino acid sequence of the growth hormone-like glycoprotein may be produced in a large amount from the above-mentioned recombinant vector using a restriction enzyme according to a conventional method and the gene thus obtained may produce a protein having the amino acid sequence of the growth hormone-like protein in a high purity and a large amount according to gene recombination techniques.

In utilizing the present gene as above, there may be employed various procedures commonly employed for usual gene recombination techniques.

The present gene may be recombined to a suitable expression vector, tranformation is carried out by introducing the recombinant vector into a suitable expression host, the resulting recombinant is incubated to induce a suitable expression, thereby producing the desired protein.

In producing the desired protein in a host using the present gene, the protein may be produced as a mature protein, namely in the form of the signal peptide removed, or alternatively the protein be produced by secretion from host cells by utilizing the said signal peptide as such or by adding any signal peptide adaptive to a suitable host cell or the like.

In this instance, initiation codon and stop codon would be required for introducing into the gene DNA sequence to be employed therefor and, where necessary, they may be added by employing any of well-known methods.

As the signal peptides adaptive to the said host cells and the like which may be preferably employed, there may be mentioned those from cellular secretory protein precursors and, for instance, those relating to gram-negative and gram-positive bacteria such as $E.\ coli$ $\beta$-lactamase, phosphated protein, alkaline phosphatase, neutral protease from the genus Bacillus and the like.

And further, expression of the said gene may be accomplished in a host cell together with, e.g. interferon, interleukin 2, proinsulin, various hormones.

In recombination of the present gene into an expression vector, there may be employed any usual methods employed for well-known gene recombination techniques, e.g. ligation with a variety of restriction enzymes.

As the expression vectors which may be utilized herein, there may be employed without specific limitation any of those capable of doing autoreplication in a host, and there may be preferably utilized those vectors wherein a replicating origin, a selective marker, a promotor, a RNA splicing site, a polyadenylated signal and the like may be involved.

As the vectors, there may be mentioned those derived from various bacteria, bacteriophage and animal virus, and there may be mentioned various viral vectors, various plasmid vectors, cosmid vector, shuttle vector and others.

As the vectors, there may be also mentioned $E.\ coli$, in particular, EK type plasmid vector, A $\lambda$ gt type phage vector, $Pseudomonas\ aeruginosa$ derived vector, $Bacillus\ subtilis$ derived vector, yeast derived vector, SV40 derived vector and the like.

As the promotor which may be employed for the above vectors, there may be mentioned those poromotors well known to those skilled in the art, such as tryptophan (trp) promotor, lactose (lac) promotor, tryptophan.lactose (tac) promotor, bacteriophage derived lambda ($\lambda$) $P_L$ promotor and others.

These gene controlling sequences may be optionally combined or chemically modified to be intergrated into a suitable vector, whereby the vector for expression of the present gene may be constructed.

Into the present gene expression vector may be further integrated plural genes of this invention to carry out expression.

The gene expression vector, which codes for the amino acid sequence of the growth hormone-like glycoprotein may be introduced into a suitable host, in particular, a host cell according to any well-known method to transform the said host cell and then the host cell thus transformed may be multiplied by incubation to obtain a large amount of the cell having a productivity of the peptide having the amino acid sequence for the growth hormone-like protein, which is referred to as "transformant".

As the host, particularly, the host cell which may be employed herein, there may be any of *E. coli;* other gram-negative bacteria than *E. coli;* gram-positive bacteria, e.g. *Bacillus subtilis* or actinomycetes; yeast; eucaryotic cell, e.g. animal and plant cells, and *E. coli* may be preferably employed.

For introduction of the present gene expression vector into the above-mentioned host and transformation there with, there may be employed any methods commonly employed in the field of gene recombination techniques, for example, admixture of competent cells with the said vector, conversion of the cell to protoplast and subsequent incorporation of the said vector bound to a carrier or coprecipitation with calcium phosphate and others.

The transformant thus obtained, after multiplication under the condition to inhibit the expression of its exogenote or vector, may induce the expression of the said exogenote or vector.

Multiplication or incubation of the transformant may be carried out by employing conventional, various media for cell culture and, as examples thereof, there may be mentioned those media which contain, e.g. carbon sources, nitrogen sources, vitamins, nucleic acid bases, inorganic salts and the like and are optionally supplemented with meat extract, peptone, Casamino acid, yeast extract, fish solubles, potato, malt extract, milk, blood, serum, hormones, antibiotics and others. Generally, commercially available media may be preferably employed as such or after suitably modified.

In multiplication or incubation of the said transformant, one may optionally determine the condition such as pH, temperature, aeration, stirring, frequency to exchange a medium and the like, which would be suitable for the growth of the said transformant.

The protein upon the expression of the present gene, which is produced by multiplication or incubation of the said transformant or by induction of the expression of the said gene, may be isolated and recovered according to usaual procedures.

As the isolation and recovery method, there may be mentioned, for example, ultrasonic disrupting of cells, mechanical mincing, freeze-drying and melting, osmotic pressure shock disrupting and others, as well as precipitation from cultured supernatant, e.g. using a protein-precipitating agent for separation.

In addition to the above-mentioned separation methods, the aimed protein may be further purified by application of various procedures for isolation and purification generally and widely employed, utilizing physiochemical or chemical properties of the protein.

As the isolation and purification methods, there may be employed precipitation with such protein-precipitating agents as ammonium sulfate as described above, as well as ultrafiltration, gel filtration, adsorption chromatography, ion exchange chromatography, affinity chromatography, high performance liquid chromatography, electrophoresis or any combination therewith.

The present growth hormone-like protein, in particular, the growth hormone-like protein derived form the pituitary gland of fishes belonging to the order Pleuronectina the family Paralichthydae can be easily confirmed for its biological activity according to the following method: Juvenile flounder are individually selected and the protein is given intraperitoneally or intramuscularly and then body weight gain and body length gain of fishes can be measured to confirm its biological activity.

A dosage for this instance may be optionally selected and determined. For example, in the case of the growth hormone-like glycoprotein isolated and purified from the flounder pituitary gland, a dose of about 0.01 $\mu$g/g of fish body weight may be given every 4 days, while, in the case of the growth hormone-like protein obtained according to gene recombination procedures, a dose of about 0.1 $\mu$g/g of fish body weight may be similarly given.

The foregoing is merely illustrative of the invention and is not intended to limit the invention to the disclosed compounds. Variations and changes which are obvious to one skilled in the art are intended to be within the scope and nature of the invention.

The transformant *Escherichia coli* fSL7, FERM P-11256 (Jan. 5, 1990); FERM BP 3295 according to the procedures described in Example 8 was deposited at the Fermentation Research Institute, Agency of Industrial Science and Technology, Ministry of International Trade and Industry, Japan (FRI) under the Budapest Treaty. Its accession numbers on the deposit dates are shown above (The deposit dates are indicated in parenthesis). As to the accession number given by FRI, FERM P number is first assigned to the domestic deposit which has been converted to the international deposit under the Budapest Treaty and the transformant has been stored at FRI under FERM BP 3295.

In the specification and drawings of the present application, the abbreviations used for bases, amino acids and so forth are those recommended by the IUPAC-IUB Commission on Biochemical Nomenclature or those conventionally used in the art. Amino acids for which optical isomerism is possible are, unless otherwise specified, in the L form.

EXAMPLE

The invention is further illustrated but in no way limited by the following examples.

EXAMPLE 1

Exatraction of flounder growth hormone-like glycoprotein

From 460 flounder aged one year were excised 3.3 g of the pituitary gland, which was immediately frozen in liquid nitrogen and then stored at a temperature of $-80°$ C. up to its use. The pituitary gland (3.3 g) was minced under ice cooling, defatted with 100 ml of ice-cooled acetone and then centrifuged at 0° C. and 15,000 rpm for 10 minutes by means of a centrifuge rotor (Hitachi Ltd., Japan, himac SCR20B). The precipitate thus obtained was suspended in 50 ml of 5 mM EDTA, the suspension was adjusted to pH 9~10 with sodium hydroxide and extracted with an alkali at 4° C. for one hour. The extract (55 ml) 5 was centrifuged at 15,000 rpm for 20 minutes by means of the above-mentioned centrifuge and the supernatant (45 ml) was dialyzed with 3 l of distilled water at 4° C. for 24 hours. The dialysate was frozen to give 483 mg of a powder.

EXAMPLE 2

Purification of flounder growth hormone-like glycoprotein

The powder obtained by Example 1 (483 mg) was dissolved in 10 ml of a 0.05M aqueous solution of ammonium acetate (pH 9.0) and the solution was fractionated through a column (2.46×63 cm) of Sephadex G-100 (Pharmacia Ltd.) equilibrated with a 0.05M aqueous solution of ammonium acetate (pH 9.0). Under elution conditions of a prestream of 200 ml and flow rate of 18 ml/hr, 4 ml of the eluate was dispensed For each test tube and the protein content was measured by determining the absorbance at 280 nm to afford 5 fractions (See, FIG. 1).

The Fraction No. 3 as shown in FIG. 1 was frozen to give 222 mg of a white powder, which was then purified by a high-performance liquid chromatography (HPLC) using a colomn (0.46×25 cm) of ODS 120T (Toso Corporation, Japan). The elution conditions for HPLC were set to be 0.1% trifluoroacetic acid, acetonitrile 20~80% linear gradients, a column temperature of 40° C. and a flow rate of 1 ml/min., the protein content was measured by determining the absorbance at 220 nm to obtain 8 mg of the flounder growth hormone-like glycoprotein (See, FIG. 2).

Figure 2:
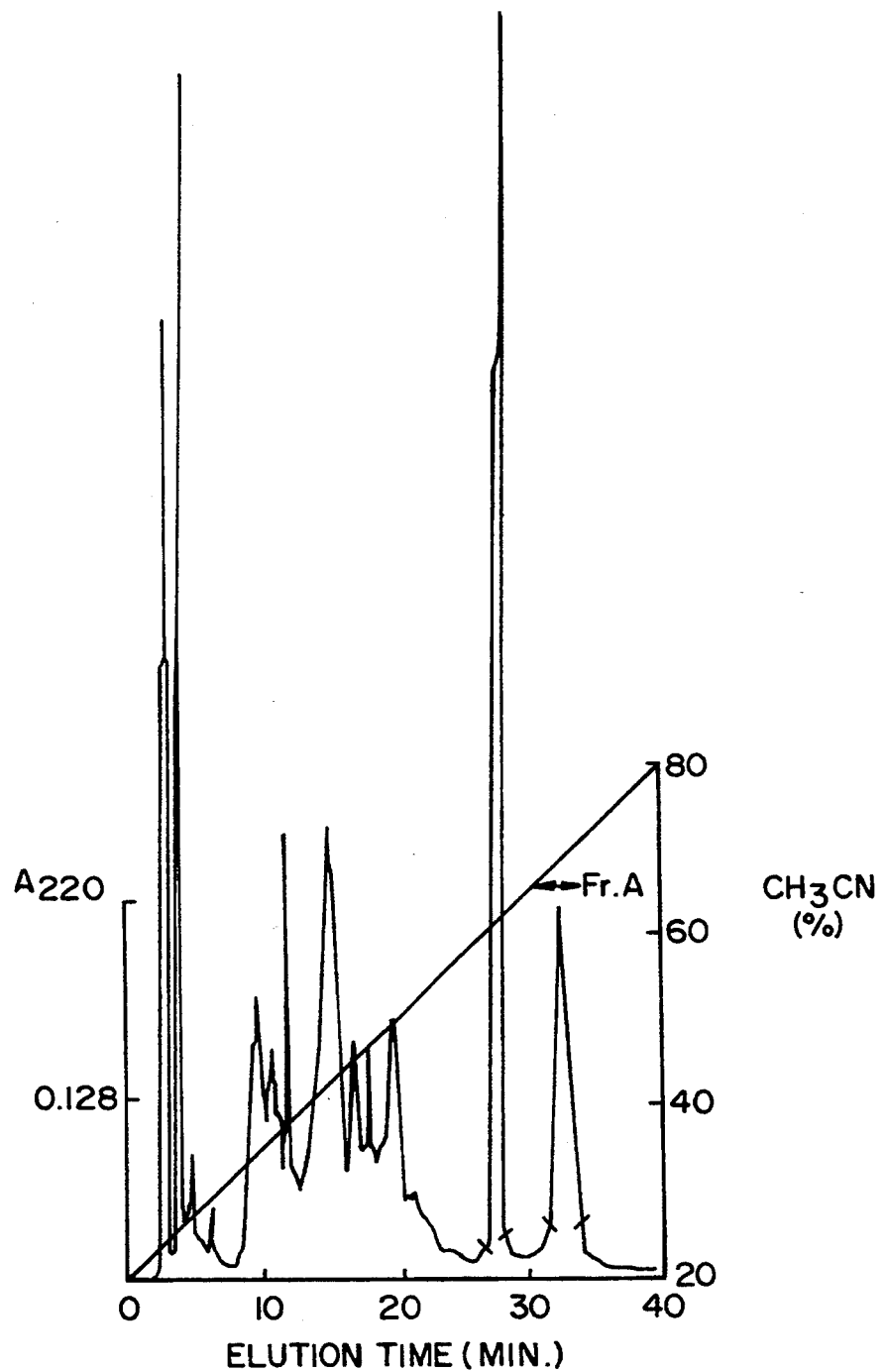
FIG. 2 shows the elution pattern for growth hormone-like glycoprotein by a high performance liquid chromatography.

The fraction A as shown in FIG. 2 had the following physicochemical properties:

EXAMPLE 3

Determination of molecular weight and isoelectric point

The fraction A obtained by Example 2 was developed by electrophoresis with SDS polyacrylamide gel to establish that the flounder growth hormone-like glycoprotein has a molecular weight of approximately 28,000 daltons (28K). In this case, one employed as a standard molecular weight marker the colored molecular weight marker LMW kit E (Pharmacia Ltd.), molecular weights 94,000; 67,000; 43,000; 30,000; 20,000; 14,000.

The fraction A obtained by Example 2 showed at the same time a single band by electrophoresis with SDS polyacrylamide gel.

The said flounder growth hormone-like was found to have an isoelectric point of 6.5 by an isolectric point gel electrophoresis.

EXAMPLE 4

Analysis of amino acid composition

The said flounder growth hormone-like glycoprotein (0.1 μg) was hydrolyzed with 20 μg of 6N hydrochloric acid containing 0.6% phenol at 110° C. for 18 hours and then amino acid were converted to the corresponding phenylthiocarbamyl derivatives with phenyl isothiocyanate (PITC) and the derivatives were quantitatively determined by a reversed-phase HPLC (PITC method). The HPLC parameter was a column TSK ODS 80T (Tosoh Corporation, Japan, 0.4×25 cm). The elution parameters were as follows: Solution A, 0.14M sodium acetate pH 5.4: acetonitrile=90:10 (containing 0.05% triethylamine), Solution B, 60% acetonitrile; initial Solution A 100%-Solution B 80%; 20 minutes; linear gradient; column temperature of 45° C.; flow rate of 1 ml/min. The amino acid composition was determined by measuring the absorbance at 254 nm.

The results are shown in the following Table.

TABLE

| Amino acid composition (residues per mole) | | | |
|---|---|---|---|
| Amino acid | Residue number | Amino acid | Residue number |
| Cys | 7.0 | Pro | 9.6 |
| Asp | 21.8 | Tyr | 6.9 |
| Glu | 30.1 | Val | 10.3 |
| Ser | 17.3 | Met | 7.6 |
| His | 6.4 | Ile | 12.0 |
| Gly | 2.9 | Leu | 29.3 |

TABLE-continued

| Amino acid composition (residues per mole) | | | |
|---|---|---|---|
| Amino acid | Residue number | Amino acid | Residue number |
| Arg | 8.9 | Phe | 6.2 |
| Thr | 8.8 | Trp | ... |
| Ala | 9.6 | Lys | 12.8 |

The said flounder growth hormone-like glycoprotein was found to show a growth hormone-like properties as it had 7 cysteines and was rich in glutamic acid, leucine and serine.

EXAMPLE 5

Determination of N-terminal amino acid sequence

The said flounder growth hormone-like glycoprotein (10 μg) was determined for its N-terminal amino acid sequence by means of a gas-phase peptide sequencer (Shimazu Corporation, Japan).

The sequence of the 23 amino acids SEQ ID NO: 1 at the N-terminal side as determined is as shown below:

Ile—Pro—Leu—Asp—Cys—Lys—
Glu—Glu—Gln—Gly—Ser—Leu—
Ser—Arg—Cys—Pro—Ser—Ile—
Ser—Gln—Glu—Lys—Leu.

EXAMPLE 6

Preparation of cDNA library of flounder pituitary gland

The whole DNA was extracted from flounder pituitary gland by employing a RNA extraction kit (Amersham Ltd.).

The flounder pituitary gland (1.0 g) was minced in 20 ml of a guanidine.thiocyanate solution (a solution comprising a guanidine.thiocyanate and 80% β-mercaptoethanol) on an ice bath, 0.3 volume of ethanol was added and the mixture was then centrifuged at 0° C. and 10,000 rpm for 5 minutes by means of a centrifuge rotor (Hitachi Ltd., Japan, himae SCR20B). The supernatant was removed, the precipitate was suspended in the abovementioned guanidine.thiocyanate, 30 ml of a lithium chloride solution was added and the mixture was allowed to stand at 0° C. for 16 hours to precipitate RNA selectively, after which it was centrifuged at 10,000 rpm for 90 minutes by means of the said centrifuge rotor. The resulting precipitate was dissolved in 35 ml of a lithium chloride solution containing urea, and centrifuged at 4° C. and 10,000 rpm for 60 minutes by means of the said centrifuge. After the supernatant was removed, the residue was dissolved in 5 ml of RNA buffer and the whole RNA was then purified, in turn, by phenol extraction (extracted twice with 5 ml of phenol, each being made at room temperature), chloroform extraction (5 ml of chloroform: isoamyl alcohol (24:1), mixed for 5 seconds) and ethanol precipitation (precipitated with 20 ml of ethanol and 5 ml of 2M sodium acetate, pH 5.0, for 16 hours and then centrifuged at 4° C. and 9,000 rpm for 30 minutes by means of the said centrifuge rotor). The resulting whole RNA was 3.6 mg.

Then, the RNA was dissolved in 1 ml of a buffer (0.5M NaCl, 20 mM Tris, 1 mM EDTA, 0.1% SDS, pH 6.7) and the SDS solution was passed through an oligo-dT-cellulose column (5-3 Prime Ltd., a column volume of 1 ml) to purify poly(A)RNA. The poly(A)RNA was obtained in a total amount of 20 μg from 1 mg of the whole RNA.

Using the poly(A)RNA thus obtained, there was carried out the synthesis of complementary DNA. The synthesis of cDNA was carried out by employing a cDNA synthesis system plus (Amersham Ltd.).

The flounder pituitary gland poly(A)RNA (5 μg) was dissolved in 25 μl of a buffer for the synthesis of 1st strand. To the solution were added, in turn, a mixture of deoxynucleoside triphosphates (containing all of dATP, dGTP, dTTP and dCTT), 2.5 μl of 0.17 OD units oligo(dT$_{12-18}$)primer and 100 units of a reverse transcriptase to make up a whole amount to 50 μl. Reaction was effected at 42° C. for 60 minutes to synthesize the DNA complementary to RNA.

Then, to 50 μl of the resulting reaction mixture were added 93.5 μl of a buffer for the synthesis of 2nd strand, 115 units of DNA polymerase in $E.$ $coli$ and 4 units of DNA ribonuclease in $E.$ $coli$ to make up a whole amount to 250 μl. Reaction was effected at 12° C. for 60 minutes and then at 22° C. for 60 minutes, and heating was applied at 70° C. for 10 minutes to stop the reaction. Ten unites of T4 DNA polymerase were added and the reaction was effected at 37° C. for 10 minutes to synthesize cDNA with blunt ends.

To the reaction mixture thus obtained were added 20 μl of 0.25M EDTA (pH 8.0) to stop the reaction. The reaction mixture was subjected to phenol-chloroform extraction (125 μl of phenol, 125 μl of chloroform, extracted twice each several minutes at room temperature) and subsequent ethanol precipitation [precipitated with 500 ml of ethanol over dry ice and then centrifuged at 12,000 rpm for 20 minutes by means of MCX-150 (Tomy Ltd.)] to produce 3 μg of cDNA.

Then, the resulting DNA complementary to the flounder pituitary gland poly(A)RNA was integrated into λ gt 10 to construct flounder pituitary gland cDNA library. In the construction of the library, one employed the cDNA cloning system λ gt 10 (Amersham Ltd.).

To 10 μg of a buffer for the methylation reaction at EcoRI site involving 1 μg of flounder pituitary gland cDNA were added 2 μl of a liquid of 20 units of EcoRI methylase and adenosyl methionine to make up a whole amount to 20 μl. Reaction was effected at 37° C. for 60 minutes and the reaction was stopped by heating the reaction mixture at 70° C. for 10 minutes.

Then, to 20 μl of the resulting reaction mixture were added 3 μl of a ligation buffer, 5 units of T4 DNA ligase and 2 μl (2 μg) of EcoRI linker to make up a whole amount to 30 μg . Reaction was effected at 15° C. for 16~20 hours to add EcoRI linker to cDNA.

Thereafter, to 3 μl of the resulting reaction mixture were added 10 μl of an EcoRI digestion buffer and 100 units of restriction enzyme EcoRI to make up a whole amount to 100 μl. Reaction was effected at 37° C. for 5 hours to form the EcoRI cohesive ends derived from EcoRI linker at the cDNA terminals.

The eluate obtained by passing the resulting reaction liquid through a gel filtration column attached to the kit was subjected to ethanol precipitation (preceitated with 800 ml of ethanol at −20° C. for 2 hours and then centrifuged at 12,000 rpm for 30 minutes by means of MCX-150 (Tomy Ltd.)) to produce cDNA having the EcoRI cohesive ends derived from EcoRI linker.

Then, to 5 μl of a liquid containing 300 ng of the resulting cDNA having the EcoRI cohesive ends derived from EcoRI linker were added 1 μl of a ligation buffer, 2.5 units of T4 DNA ligase and 2 ml (1 μg) of λ gt 10 EcoRI fragment to make up a whole amount to 10 μg. Reaction was effected at 150° C. for 16–20 hours to synthesize the λ gt 10 DNA vector integrated with the said flounder pituitary gland cDNA.

The recombinant λ gt 10 DNA vector thus obtained was subjected to in vitro packaging by the in vitro packaging extract attached to the kit to produce the flounder pituitary gland cDNA library having an efficiency of $3.3 \times 10^5$ recombinants/μg cDNA in $E.$ $coli$ NM514.

EXAMPLE 7

Selection of flounder growth hormone-like glycoprotein cDNA

For selection of the flounder growth hormone-like glycoprotein cDNA from the flounder pituitary gland cDNA library, one employed as probe the synthetic DNA corresponding to the 5th to 22nd amino acid sequence in the N-terminal amino acid sequence of the said flounder growth hormone-like glycoprotein (prepared by means of a DNA synthesis apparatus, Model 381A Synthesizer, Applied Biosystems Ltd.). It has the following base sequence:

```
3'
A C A T T C C T C C T C G T C C C G A G G G A C
    G       T T
A G G G C C A C G G G G A G G T A G A G G G T C C
                                            T
      5'
T C T T
T
```

The said probe was used by marking with [Tδ-$^{32}$P]dATP and T4 polynucloetide kinase.

The library ($2 \times 10^4$ pfu) obtained by Example 6 was infected with 50 μl $E.$ $coli$ NMB514, which was incubated on LB medium for 16 hours, layered over a LB plate with 9 cm, the DNA of the plaque thus formed was fixed on a nylon filter and plaque hybridization was effected according to the Maniatis et. al. method [Molecular Cloning (1982)].

The probe was washed four times with 1XSSC (0.15M NaCl, 0.015M sodium citrate) 0.1% SDS liquid at 55° C. for every 10 minutes and then twice at 60° C. for every 10 minutes to select the plaque corresponding to that having tightly bound to the said marking probe, whereby there were obtained 29 clones having cDNA of the said flounder growth hormone-like glycoprotein.

EXAMPLE 8

Determination of base sequence of cDNA in growth hormone-like glcyoprotein

From 29 of the recombinant phages obtained by Example 7 was isolated the recombinant λ gt 10 DNA having cDNA of the said flounder growth hormone-like glycoprotein was then isolated by EcoRI treatment. The length thereof was investigated to show that 9 clones have 1.0 Kb and the remaining 20 clones have 1.6 Kb. The resulting cDNA of growth hormone-like glycoprotein was digested with various restriction enzymes (XbaI, EcoRV, PstI, StuI, Bgi II, SmaI) to prepare a restriction map (See, FIG. 3).

Thus, the resulting 20 clones having 1.6 Kb and the 20 clones having 1.0 Kb have been found to have the identical restriction maps, respectively. Then, one clone each of the 1.0 Kb and 1.6 Kb clones was selected [cfSL3 (1.0 Kb), cfSL7 (1.6 Kb)] and the whole base sequence was determined according to Sanger method [Sanger et al., (1977), Pro. Natl. Acad. Sci. U.S.A., 74, 5463–5467].

Figure 3:
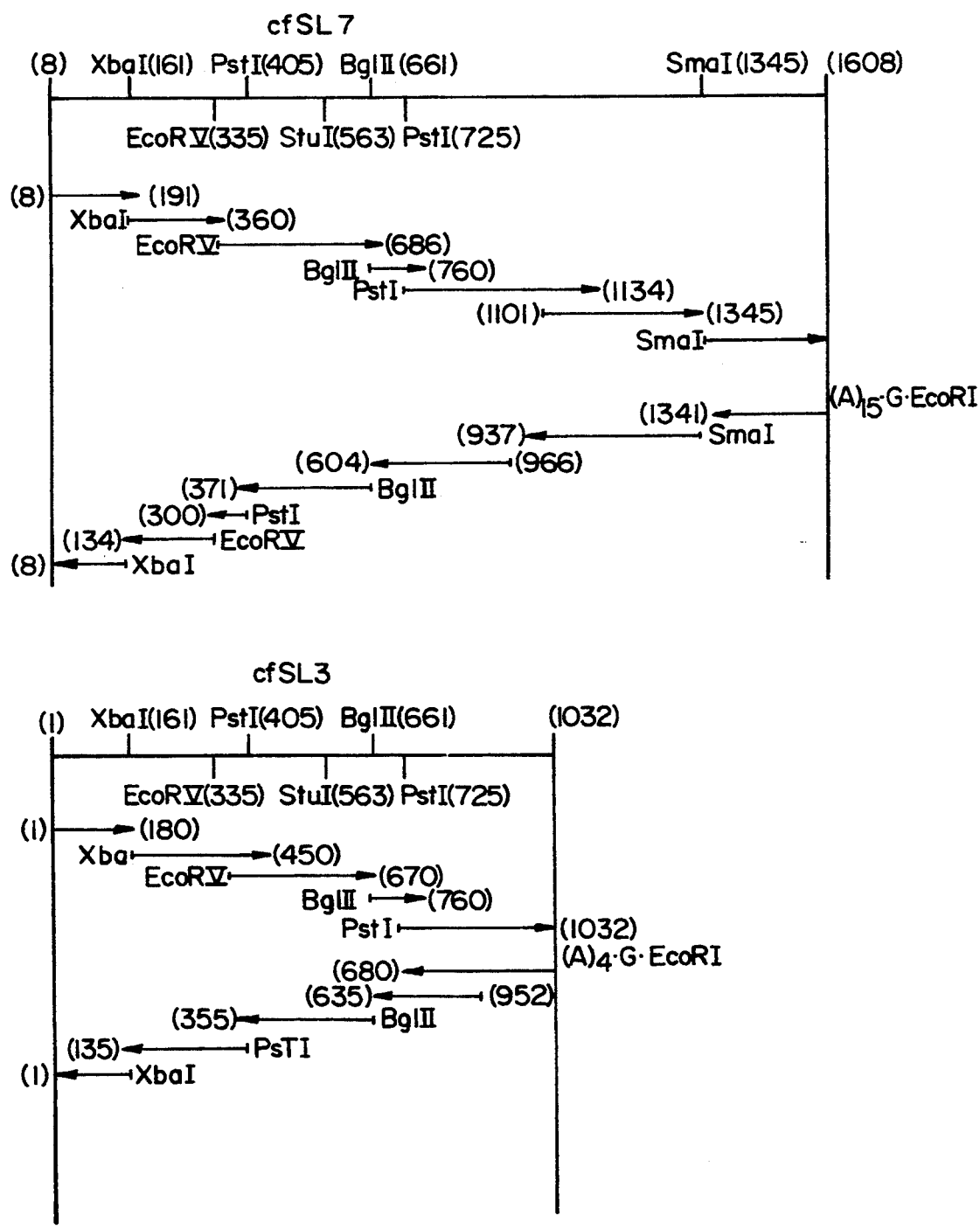
FIG. 3 shows restriction maps and sequence strategies for the gene coding the amino acid sequence of growth hormone-like glycoprotein, wherein the figure in parenthese ( ) shows the base number from 5′ terminal.
Figure 5:
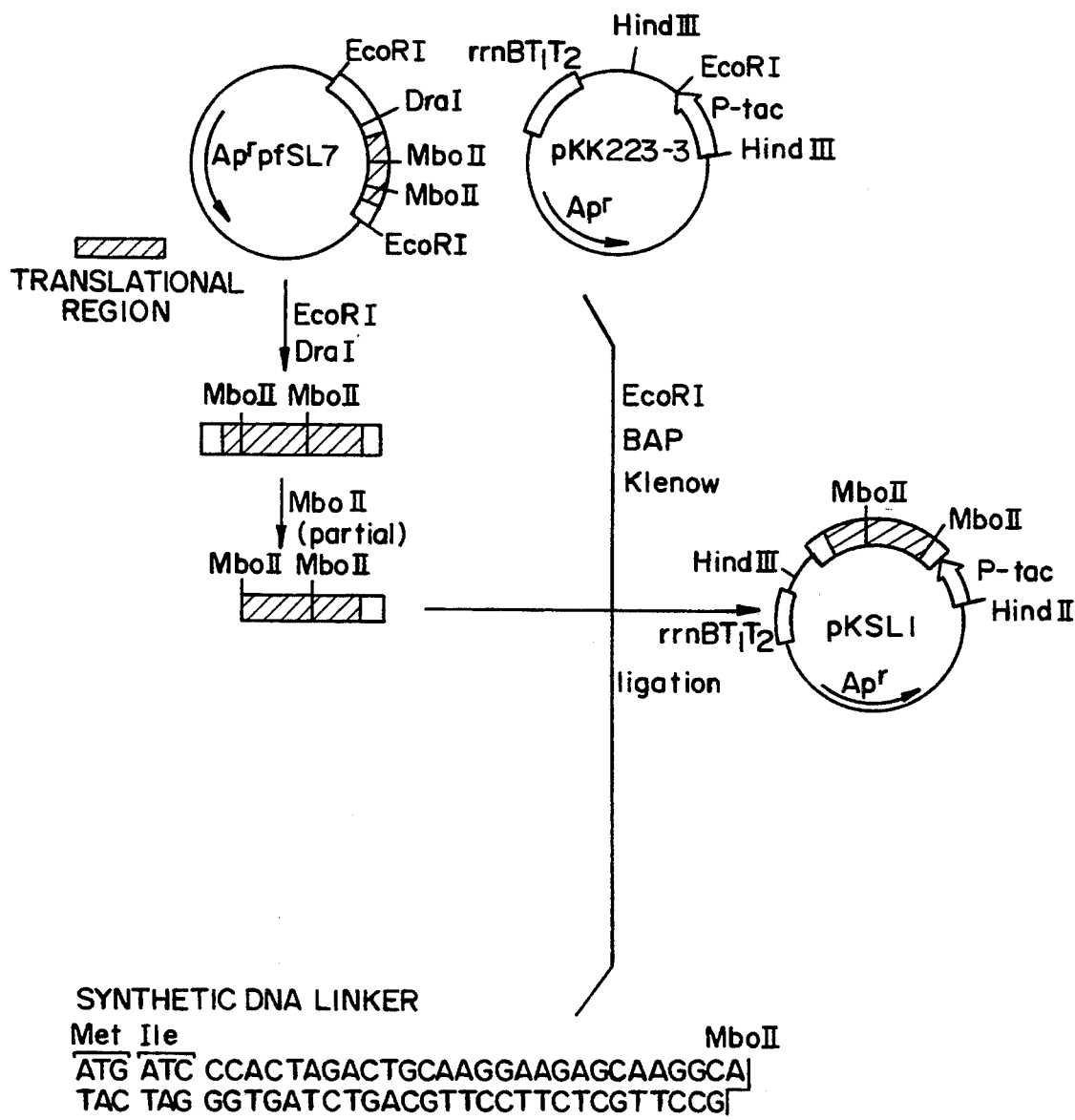
FIG. 5 shows the procedures for constructing recombinant plasmid pKSL1.

The strategy for determination of base sequence is shown in FIG. 3.

Determination of base sequence was carried out by forming deletion mutants with digestion by restriction enzymes and, if no restriction enzyme site is found, by synthesizing primers.

The base sequence of the flounder growth hormone-like glycoprotein is as shown in FIG. 4 as SEQ ID NO: 4.

The glycoprotein cDNA's of cfSL3 and cfSL7 as obtained above had the identical 5'-terminal sides and cfSL7 had the 577 bp sequence added at the 3'-terminal as compared with cfSL3.

Of the base sequence as shown in FIG. 4, the sequence of the base number of 1~72 codes signal peptide, while the sequence of the base number of 73~693 does a mature protein of the said growth hormone-like glycoprotein.

Further, the said maturation protein has been found to have sugar-chain addition sequences of Asn, Lys and Thr at the amino acid residue numbers of 121, 122 and 123, respectively. The maturation protein had an amino acid residue number of 207 and a molecular weight of 23,996 daltons (24K). In view of the molecular weight of 28K in Example 3, the sugar chain having a molecular weight of approximately 400 daltons is seen to be bound to the said sugar chain addition site.

This cDNA base sequence is in complete agreement with the base sequence as expectable from the determined amino acid sequence of the said growth hormone-like glycoprotein, and the said cDNA has been confirmed to code the amino acid sequence and the sugar chain addition site of the said growth hormone-like glycoprotein previously determined from the flounder growth hormone-like glycoprotein.

The *E. coli* in which the plasmid pfSL7 containing cfSL7 is habored has been deposited as *Escherichia coli* fSL7 in the Fermentation Research Institute, Agency of Industrial Science and Technology, Japan. and given accession number FERM P-11256 (Jan. 5, 1990).

The base sequence of this cDNA has a significant homology with those growth hormones such as prolactin and the like and, in particular, a significant homology has been observed with the growth hormone of rats, mammals. This cleary shows that the said growth hormone-like glycoprotein has a similar activity to growth hormone.

EXAMPLE 9

Preparation of recombinant plasmid coding for flounder growth hormone-like glycoprotein The plasmid pfSL7 (5 μg) containing DNA coding for flounder growth hormone-like glycoprotein was dissolved in 20 μl of a reaction liquid (hereinafter referred to as "H Buffer") which comprised 100 mM Tris HCl (pH 7.5), 7 mM MgCl₂, 50 mM NaCl, 7 mM 2-mercaptoethanol, and 100 μg/ml bovine serum albumin, 30 units each of the restriction enzymes EcoRI and DraI (Toyobo Co., Ltd., Japan) was added and reaction was effected at 37° C. for 2 hours. The reaction mixture was extracted with phenol, the portion, which coded the amino acid sequence of the flounder growth hormone-like glycoprotein of approximately 700 bp, was cut out by agarose gel electrophoresis, DNA was recovered by a kit for DNA purification, Geneclean (Funakoshi Yakuhin K.K., Japan). After precipitation with ethanol, it was dissolved in 20 μl of a mixture of 70 mM Tris.HCl (pH 7.5), 10 mM KCl, 7 mM MgCl₂, 7 mM 2-mercaptoethanol and 10 ng/bovine serum albumin, 5 units of the restriction enzyme Mbo II (Toyobo Co., Ltd., Japan) were added and reaction was effected at 37° C. for 10 minutes. The reaction mixture was subjected to agarose gel electrophoresis to cut out the Mbo II partially digested fragment of about 650 bp, which gave by the said kit for purification of DNA about 0.1 μg of the fragment of approximately 650 bp which involved a translation region of mature flounder growth hormone-like glycoprotein coded at cfSL7 DNA and a 3' flanking region.

Separately, a prokaryote expression vector (Pharmacia Ltd.) was dissolved in H Buffer, 20 units of the restriction enzyme EcoRI (Toyobo Co., Ltd., Japan) were added and reaction was effected at 37° C. for one hour. After precipitation with ethanol, the reaction mixture was dissolved in 50 μl of a mixture of 67 mM KPO₄ (pH 7.4), 6.7 mM MgCl₂, 1 mM 2-mercaptoethanol, 33 μM dNTT (dATP, dCTP, dGTP, dTTP), 20 units of Klenow fragment (Toyobo Co., Ltd., Japan) were added and reaction was effected at room temperature for 30 minutes. After addition of one unit of alkaline phosphatase (BAP) (Toyobo Co., Ltd., Japan), was effected at 0° C. for 30 minutes. The reaction mixture was extracted with chloroform and DNA was recovered by ethanol precipitation.

Then, two oligonucleotides (34, 44 oligonucleotides) containing initiation codon (ATG) and 5-terminal ATC (Ile) to Mbo II restriction site were synthesized by using the synthesizer Model 381A (Applied Biosystms Co.).

The oligonucleotide 34 (2 μg) was dissolved in 50 μl of a solution of 50 mM Tris HCl (pH 7.6), 10 mM MgCl₂, 10 mM 2-mercaptoethanol and 100 nM ATP, 10 units of T4 polynucleotide kinase (Toyobo Co., Ltd., Japan) was added and reaction was effected at 37° C. for 30 minutes. After treatment with phenol, the unreacted ATP was removed by a Sephadex G-50 (Pharmacia Ltd.) column (a volume of 0.9 ml). The phosphonylated oligonucleotide 34 and the previously synthesized oligonucleotide 33 were dissolved in TE buffer [10 mM Tris HCl (pH 7.6), 10 mM EDTA], the solution was heated at 75° C. for 5 minutes and then cooled slowly up to room temperature to prepare a DNA linker having the following sequence SEQ ID NO: 5.

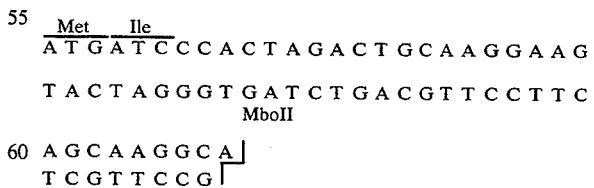

The Mo II-Dra I fragment of cfSL7 obtained as above (0.1 μg), the phosphorylated pKK223-3 EcoRI fragment (0.7 μg) and the DNA linker (0.5 μg) were dissolved in 10 μl of TE buffer and ligation reaction was effected by the use of a ligation kit (Takara Shuzo K.K., Japan). By employing the said reaction liquid, competent *E. coli* JM104 strain cells (Takara Shuzo K.K., Japan) were transformed and the colonies grown well on LB plates containing ampicillin were selected to obtain the plasmid pKgL1 coding the amino acid sequence of mature flounder growth hormone-like glycoprotein.

EXAMPLE 10

Production of flounder growth hormone-like glycoprotein by *E. coli* containing pkSL1

Using the recombinant plasmid pkSL]obtained by Example 9, *E. coli* JM109 strain was transformed in a conventional manner. The resulting ampicillin-resistant colony was inoculated to 10 ml of MGG medium (0.6% $Na_2HPO_4$, 0.3% $KH_2PO_4$, 0.5% NaCl, 0.1% $NH_4Cl$, 0.5% glucose, 0.5% Casamino acid, 1 mM $MgSO_4$, 4 ng/ml Vitamin $B_1$, pH 7.2) and incubated at 37° C. for 16 hours. The resulting cultured broth was inoculated to 1 l of the MMG medium and incubated at 37° C. for 16 hours. Thereafter, the resulting cultured broth was centrifuged at 8,000 rpm for 10 minutes by means of a centrifuge rotor (himac SCR 20B, Hitachi, Ltd., Japan) to recover micro-organisms.

The micro-organisms were suspended in Laemmli Sample Buffer [Laemmli, U. K. (1970), Nature (London), 227, 680–685] and a direct SDS polyacrylamide gel electrophoresis was effected. The Western blotting [Towbin et al., (1979), Proc. Natl. Acad. Sci. U.S.A., 76, 350] using rabbit antibody was effected for the flounder growth hormone-like glycoprotein extracted from flounder pituitary gland. As a result, a band crossing the flounder growth hormone-like glycoprotein antibody was observed at the site of a molecular weight of approximately 24,000 daltons. There results can clearly show that *E. coli* having pkSL1 surely produces in a large amount the flounder growth hormone-like glycoprotein.

EXAMPLE 11

Preparation of recombinant flounder growth hormone-like protein

Following the procedures in Example 10, a microorganism capable of producing flounder growth hormone-like protein was incubated and harvested, a flounder growth hormone-like protein in inclusion bodies was obtained according to Marston method (DNA cloning; A Practical Approach (Ed. by D. M. Glover), (1987) 3, 59, IRL Press, Oxford). Further, the flounder growth hormone-like protein was extracted according to Schoner et al. method (Bio/Tech (1985), 3, 151), regenerated and purified by HPLC to obtain 20 mg of the recombinant flounder growth hormone-like protein.

EXAMPLE 12

Determination of physiological activity

Flounders aged 4 months after hatching (10–15 g), a group consisting of 10 fishes, were individually selected and intraperioneally given the fraction A obtained by Example 2, i.e. the said flounder growth hormone-like glycoprotein; the recombinant flounder growth hormone-like glycoprotein obtained by Example 11; and, as a control, physiologial saline every 4 days at 0.01 µg and 0.1 µg/gram of fish body weight, respectively.

Fish breeding was carried out at 20° C. and feed (Nihon Haigoshiryo K.K., Japan) was given in a 1.5 % amount to the body weight of juvenile flounder in a divided from twice mornings and evenings. Body weight gain rates on the 35th day from the first administration are shown in Table 2.

As apparent from Table 2, the growth hormone-like protein according to this invention has been found to be effective in growth promotion of fishes such as flounders and so on.

TABLE 2

| Sample | Body weight gain (%) |
| --- | --- |
| Physiological saline | 15 |
| Growth hormone-like glycoprotein 0.01 µg | 30 |
| Recombinant growth hormone-like protein 0.1 µg | 41 |

---

What is claimed is:

1. A protein having fish growth promoting activity wherein said protein has the following physicochemical properties:

(1) Molecular weight: SDS-PAGE about 28,000 daltons,
(2) Isoelectric point: Isoelectric point-PAGE 6.5,
(3) Amino acid composition (residues per mole)

| Amino Acid | Residue Number |
|---|---|
| Cys | 7.0 |
| Asp | 21.8 |
| Glu | 30.1 |
| Ser | 17.3 |
| His | 6.4 |
| Gly | 2.9 |
| Arg | 8.9 |
| Thr | 8.8 |
| Ala | 9.6 |
| Pro | 9.6 |
| Tyr | 6.9 |
| Val | 10.3 |
| Met | 7.6 |
| Ile | 12.0 |
| Leu | 29.3 |
| Phe | 6.2 |
| Trp | ... |
| Lys | 12.8 |

(4) 23 Amino acid residues at N-terminal end having the following sequence SEQ ID NO: 1:

Ile—Pro—Leu—Asp—Cys—Lys—
Glu—Glu—Gln—Gly—Ser—Leu—
Ser—Arg—Cys—Pro—Ser—Ile—
Ser—Gln—Glu—Lys—Leu.

2. The protein of claim 1 wherein said protein is obtained by extraction and purification from the pituitary gland of fishes belonging to the order Pleuronectina, the family Paralichthydae.

3. A protein having fish growth promoting activity and comprising the following amino acid sequence SEQ ID No: 2:

| Ile 1 | Pro | Leu | Asp | Cys | Lys |
| Glu | Glu | Gln | Gly 10 | Ser | Leu |
| Ser | Arg | Cys | Pro | Ser | Ile |
| Ser | Gln 20 | Glu | Lys | Leu | Leu |
| Asp | Arg | Val | Ile | Gln | His 30 |
| Ala | Glu | Leu | Ile | Tyr | Arg |
| Val | Ser | Glu | Glu 40 | Ser | Cys |
| Ser | Met | Phe | Glu | Glu | Met |
| Phe | Val 50 | Pro | Phe | Pro | Leu |
| Arg | Leu | Gln | Arg | Asn | Gln 60 |
| Ala | Gly | Tyr | Ala | Cys | Ile |
| Thr | Lys | Ala | Leu 70 | Pro | Ile |
| Pro | Ser | Ser | Lys | Ser | Glu |
| Ile | Gln 80 | Gln | Ile | Ser | Asp |
| Thr | Trp | Leu | Leu | His | Ser 90 |
| Val | Leu | Met | Leu | Val | Gln |
| Ser | Trp | Ile | Glu 100 | Pro | Leu |
| Val | Tyr | Leu | Gln | Thr | Thr |
| Leu | Asp 110 | Arg | Tyr | Asp | Asn |
| Ala | Pro | Asp | Met | Leu | Leu 120 |
| Asn | Lys | Thr | Lys | Trp | Val |
| Ser | Asp | Lys | Leu 130 | Ile | Ser |
| Leu | Glu | Gln | Gly | Val | Val |
| Val | Leu 140 | Ile | Arg | Lys | Met |
| Leu | Asp | Glu | Gly | Met | Leu 150 |
| Thr | Ala | Thr | Tyr | Asn | Glu |
| Gln | Gly | Leu | Phe 160 | Gln | Tyr |
| Asp | Ala | Gln | Pro | Asp | Met |
| Leu | Glu 170 | Ser | Val | Met | Arg |
| Asp | Tyr | Thr | Leu | Leu | Ser 180 |
| Cys | Phe | Lys | Lys | Asp | Ala |
| His | Lys | Met | Glu 190 | Ile | Phe |
| Leu | Lys | Leu | Leu | Lys | Cys |
| Arg | Gln 200 | Thr | Asp | Lys | Tyr |
| Asn | Cys | Ala. 207 | | | |

4. A protein having fish growth promoting activity and comprising the amino acid sequence SEQ ID No: 3 in FIG. 4.

* * * * *

UNITED STATES PATENT AND TRADEMARK OFFICE
CERTIFICATE OF CORRECTION

PATENT NO. : 5,359,036          Page 1 of 3
DATED : October 25, 1994
INVENTOR(S) : Shusaku Sakata, et al.

It is certified that error appears in the above-indentified patent and that said Letters Patent is hereby corrected as shown below:

Column 2, line 22: "G-J00" should read --G-100--
Column 2, line 35: after "rectangle" insert
-- ▭ --
Column 4, line 38: "SEQUID" should read --SEQ ID--
Column 5, line 25: "G-J00" should read --G-100--
Column 5, line 45: "SDB" should read --SDS--
Column 6, line 68: "3153" should read --3143--
Column 7, line 68: "Barget" should read --Barger--
Column 9, line 13: "SEQUID" should read --SEQ ID--
Column 10, line 42: delete "A"
Column 13, line 3: "For" should read --for--
Column 13, line 44: "µg" should read --µ$\ell$ --
Column 13, line 44: "6N" should read --6 N--

Column 14, line 42: "himae" should read --himac--
Column 15, lines 40 & 50: "µg" should read
--µ$\ell$ --

UNITED STATES PATENT AND TRADEMARK OFFICE
CERTIFICATE OF CORRECTION

PATENT NO. : 5,359,036  
DATED : October 25, 1994  
INVENTOR(S) : Shusaku Sakata, et al.

Page 2 of 3

It is certified that error appears in the above-indentified patent and that said Letters Patent is hereby corrected as shown below:

Column 16, line 2: "µg" should read --µℓ--  
Column 16, line 2: "150°" should read --15°--  
Column 16, lines 26-36:

```
         3'
"  A C A T T C C T C C T C G T C C C G A G G G A C     "
   G     T   T
 A G G G C C A C G G G G A G G T A G A G G G T C C
                                             T
         5'
 T C T T
   T
``` should read:

```
          3'
     A C A T T C C T C C T C G T C C C G A G G G A C
       (G)  (T) (T)
     A G G C C A C G G G G A G G T A G A G G G T C C
            5'                                  (T)
     T C T T
        (T)
```

UNITED STATES PATENT AND TRADEMARK OFFICE
CERTIFICATE OF CORRECTION

PATENT NO. : 5,359,036
DATED : October 25, 1994
INVENTOR(S) : Shusaku Sakata, et al.

It is certified that error appears in the above-indentified patent and that said Letters Patent is hereby corrected as shown below:

Column 16, line 38: "[T6" should read --[γ--
Column 16, line 41: "NMB514" should read --NM514--
Column 16, line 58: "glcyoprotein" should read --glycoprotein--
Column 18, line 13: "H" should read --II--
Column 19, line 4: "pKgL1" should read --pKSL1--
Column 19, line 12: "pkSL]" should read --pKSL1--
Column 19, line 19: "1 1" should read --1 ℓ --
Column 19, line 29: "350" should read --4350--

Signed and Sealed this

Sixth Day of June, 1995

BRUCE LEHMAN

Attest:

Attesting Officer

Commissioner of Patents and Trademarks